US010966983B2

(12) United States Patent
Aoki et al.

(10) Patent No.: US 10,966,983 B2
(45) Date of Patent: Apr. 6, 2021

(54) COMPOSITION FOR EXTERNAL USE

(75) Inventors: Akihiro Aoki, Osaka (JP); Kosaburo Wakamatsu, Osaka (JP); Shigeo Shinohara, Osaka (JP); Osamu Takasu, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 12/996,929

(22) PCT Filed: Apr. 22, 2009

(86) PCT No.: PCT/JP2009/058022
§ 371 (c)(1),
(2), (4) Date: Dec. 8, 2010

(87) PCT Pub. No.: WO2009/150902
PCT Pub. Date: Dec. 17, 2009

(65) Prior Publication Data
US 2011/0081429 A1 Apr. 7, 2011

(30) Foreign Application Priority Data

Jun. 9, 2008 (JP) .............................. JP2008-150847
Aug. 29, 2008 (JP) .............................. JP2008-222246

(51) Int. Cl.
| A61K 36/00 | (2006.01) |
| A61K 31/52 | (2006.01) |
| A61K 36/75 | (2006.01) |
| A61K 8/92 | (2006.01) |
| A61Q 19/02 | (2006.01) |
| A61K 8/49 | (2006.01) |
| A61Q 19/00 | (2006.01) |
| A61K 8/60 | (2006.01) |
| A61K 36/53 | (2006.01) |

(52) U.S. Cl.
CPC ............ *A61K 31/52* (2013.01); *A61K 8/4953* (2013.01); *A61K 8/606* (2013.01); *A61K 8/922* (2013.01); *A61K 36/53* (2013.01); *A61K 36/75* (2013.01); *A61Q 19/00* (2013.01); *A61Q 19/007* (2013.01); *A61Q 19/02* (2013.01)

(58) Field of Classification Search
CPC ...... A61K 36/15; A61K 36/185; A61K 36/28; A61K 36/53; A61K 36/14; A61K 36/67; A61K 36/79
See application file for complete search history.

(56) References Cited

U.S. PATENT DOCUMENTS

| 6,946,436 | B2 | 9/2005 | Wakamatsu et al. | |
| 7,557,093 | B2 | 7/2009 | Shinohara et al. | |
| 7,820,636 | B2 | 10/2010 | Okuda et al. | |
| 2004/0029761 | A1 | 2/2004 | Wakamatsu et al. | |
| 2005/0014730 | A1* | 1/2005 | Carlson et al. | 514/169 |
| 2005/0222076 | A1 | 10/2005 | Kawamura et al. | |
| 2006/0100287 | A1 | 5/2006 | Okajima et al. | |
| 2006/0159639 | A1* | 7/2006 | Ogura et al. | 424/65 |
| 2006/0216251 | A1* | 9/2006 | Morariu | 424/59 |
| 2006/0287390 | A1 | 12/2006 | Sagawa et al. | |
| 2007/0135374 | A1 | 6/2007 | Shinohara et al. | |
| 2007/0219158 | A1* | 9/2007 | Aoki et al. | 514/54 |
| 2007/0232560 | A1* | 10/2007 | Dobson et al. | 514/46 |
| 2007/0280979 | A1 | 12/2007 | Shinohara et al. | |

FOREIGN PATENT DOCUMENTS

| CN | 1429540 | | 7/2003 |
| CN | 1456212 | A | 11/2003 |
| CN | 1503655 | | 6/2004 |
| DE | 200 22 691 | U1 | 2/2002 |
| EP | 1 547 577 | A1 | 6/2005 |
| JP | 03-255031 | | 11/1991 |
| JP | 2001-288046 | | 10/2001 |
| JP | 2002-510608 | | 4/2002 |
| JP | 2002-510610 | | 4/2002 |
| JP | 2002-234830 | | 8/2002 |
| JP | 2003-081840 | | 3/2003 |
| JP | 2004-323401 | A | 11/2004 |
| JP | 2006-151971 | | 6/2006 |
| JP | 2006-182746 | | 7/2006 |
| JP | 2006-225271 | A | 8/2006 |
| KR | 2003-0024322 | | 3/2003 |
| WO | WO-2003/084485 | A1 | 10/2003 |
| WO | WO 2005/034902 | A1 | 4/2005 |

(Continued)

OTHER PUBLICATIONS

Harborne et al. (2002) Phytochemistry of the genus *Lavandula*. In Lavender: The genus *Lavandula*. Ed. Maria Lis-Balchin. Taylor & Francis, London and New York. pp. 86-99.*
Kalemba et al. (2003) Curr. Med. Chem. 10, pp. 813-829.*
Cavanagh et al. (2002) Phytother. Res. 16, pp. 301-308.*
Janssen et al. (1988) Pharmaceutisch Weekblad Scientific Edition. vol. 10 pp. 277-280.*
Lorenc-Plucinska et al. (2003) Acta Physiologiae Plantarum vol. 25., No. 1. pp. 19-29.*
Shellie et al. (2002) J. Chromatography A, 970, pp. 225-234.*
Singh et al. (2006) J. Sci. Food Agric. 86, pp. 111-121.*
Lawless, J. (2002) The Encyclopedia of Essential Oils. (Thorsons, London) pp. 115-118.*
Wang et al. (2011) J. Ethnopharmacology 136: 10-20.*
Website document entitled "Essential Oil Co.—Star Anise Oil". (available at http://www.essentialoilco.com/star-anise-oil.html) Downloaded Mar. 30, 2012.*

(Continued)

*Primary Examiner* — Russell G Fiebig
(74) *Attorney, Agent, or Firm* — Finnegan, Henderson, Farabow, Garrett & Dunner, LLP

(57) ABSTRACT

The present invention provides an externally applied composition capable of enhancing a stimulatory effect of an essential oil on IGF-1 secretion, the composition including (A) essential oil; and (B) at least one member selected from the group consisting of purine substances and salts thereof. Further, the present invention provides an externally applied composition capable of increasing the stratum corneum water content of the skin and maintaining transepidermal water loss at an appropriate level.

7 Claims, 14 Drawing Sheets

(56) References Cited

FOREIGN PATENT DOCUMENTS

| WO | WO-2007/074602 A1 | 7/2007 |
|---|---|---|
| WO | WO 2008/049651 A1 | 5/2008 |

OTHER PUBLICATIONS

Website document entitled "Esoteric Oils: Pine essential oil and pine needle essential oil information" (available at http://www.essentialoils.co.za/essential-oils/pine.htm) Downloaded from website Aug. 31, 2015.*
Website document entitled "Essential Oi Co.—Pine Oil" (available at http://www.essentialoilco.com/pine-oil.html). Downloaded from website Mar. 30, 2015.*
Kosalec et al. (2005) Acta Pharm. 55: 377-385.*
De et al. (2002) Phytother. Res. 16, 94-95.*
Website document entitled: "Clean Essence: Star Anise Soup" (available at http://cleanessencesoaps.com/StarAnise.htm). downloaded from website Jan. 20, 2015.*
Bolinder et al. (1957) Acta Chem Scan. 11 No. 9, 1610-1612.*
Janssen et al. (1986) Phamaceutisch Weekblad Scientific Edition, vol. 8, pp. 289-292.*
Hammer et al. (1999) J. Applied Microbiology 86, 985-990.*
Singh et al. (2006) J. Sci. Food Agric. 86: 111-121.*
International Search Report from the Japanese Patent Office for International Application No. PCT/JP2009/058022 (dated Jun. 16, 2009).
Supplementary European Search Report for corresponding EP Application No. 09762333.4 dated Nov. 14, 2013.
Harada, Naoaki et al., "Effect of topical application of capsaicin and its related compounds on dermal insulin-like growth factor-I levels in mice and on facial skin elasticity in humans," *Growth Hormone & IGF Research* 17 (2007) 171-176.
Shin, Joseph et al., "Parathyroid Hormone-related Protein Enhances Insulin-like Growth Factor-I Expression by Fetal Rat Dermal Fibroblasts," *The Journal of Biological Chemistry*, vol. 272, No. 38, pp. 23498-23502 (1997).
Gao Yi et al., "Study on Optimum Process for Extracting Capsicum in Paprika (*Capsicum Annuum* L.) by Orthogonal Test," Chemistry and Industry of Forest Products, vol. 25, No. 2, Jun. 2005, pp. 111-114.
Office Action for corresponding EP Patent Application No. 09762333.4 dated Feb. 10, 2016.
Save the Males Multi-Benefit Moisturizer Moisturizing, Mintel Database, Jun. 2007, http://www.gnpd.com.
Extended European Search Report dated May 7, 2018 for correspond EP Patent Application No. 18150042.2.

* cited by examiner

Non-application site
after the eighth week
of the experiment

Application test site
after the eighth week of
the experiment

COMPOSITION FOR EXTERNAL USE

TECHNICAL FIELD

The present invention relates to an externally applied composition containing an essential oil and a purine substance and/or a salt thereof.

BACKGROUND ART

Various types of skin-aging phenomena are caused by diverse factors, such as aging, sunlight (ultraviolet radiation) exposure, eating habits and stress. Examples of skin-aging phenomena include pigmentation that produces skin problems such as blemishes, freckles and chloasmas, skin dullness, dryness and wrinkles. Prevention of such skin aging is a great health and aesthetic concern, particularly for women.

Essential oils are known as organic compounds that contain volatile aromatic substances found in plants. Commonly, essential oils are used as fragrances. Essential oils are also known for their antibacterial and antifungal effects and periodontal disease-preventive effects (Patent Document 1). However, the effects of application of essential oils on the skin are not well known.

An o/w-type composition containing substances such as adenine is known as a means to reverse skin aging (Patent Document 2 and 3). Purine substance are known to stimulate skin turnover by increasing the intracellular ATP level and prevent pigmentation such as blemishes and chloasma.

Additionally, flexibility, elasticity and water-holding ability are also related to skin-aging prevention. Their levels drop due to aging, stress and other various external factors. An IGF-1 (insulin-like growth factor-1) is known as a protective factor that contributes to the maintenance or improvement of flexibility, elasticity and water-holding ability. However, the ability of purine substances to stimulate IGF-1 secretion is yet unknown.

With the recent trend toward more diverse and advanced physiological effects required for compositions for external use, there has been a demand for the development of an externally applied composition that exerts further multifaceted effects on the skin.

Such an externally applied composition is also expected to provide an effect of creating a fresh-looking skin. The skin consists of the epidermis (top layer), dermis (deep layer) and subcutaneous tissue, and the stratum corneum is present on the outermost surface of the epidermis. The stratum corneum, formed by epidermal cells, acts as a barrier between the external environment and the inside of the body. The quality of the stratum corneum is the crucial factor in determining the freshness of the skin. The stratum corneum contains substances such as intercellular lipids and natural moisturizing factors (NMF). The stratum corneum not only prevents water evaporation from inside the skin, but also maintains the flexibility and smoothness of the skin surface by retaining an adequate amount of water in the stratum corneum itself. This important quality of stratum corneum is evaluated using "stratum corneum water content", which indicates the water-holding ability of the stratum corneum, and "transepidermal water loss (TEWL)", which indicates the amount of water that evaporates from the surface of the stratum corneum.

Along with aging, the skin undergoes various characteristic changes such as atrophy of the epidermis, thickening of the stratum corneum and loss of the granular layer that is present below the stratum corneum. Aged skin having such above-described characteristics has a low stratum corneum water content compared to younger skin, and the level of TEWL also tends to decline. It is known that dry ambient air roughens the surface of such aged skin, and is accompanied by light chapping and itching. A conventional skin cream preserves the stratum corneum surface and thereby suppresses evaporation from the skin. Although a temporal increase in the stratum corneum water content can be expected from the conventional skin cream, its effect immediately disappears once the use is discontinued. This is because of a low amount of moisture supply from the inside to the stratum corneum, i.e., low moisture penetration. Thus, maintenance of a youthful and healthy skin condition requires maintenance of an appropriate level of TEWL in addition to an increase in the stratum corneum water content accomplished by normalizing the function of the stratum corneum. Accordingly, there has been a demand for a composition that works for both the TEWL and stratum corneum water content.

CITATION LIST

Patent Literature

Patent Document 1: Japanese Unexamined Patent Publication No. 3-255031
Patent Document 2: Japanese Unexamined Patent Publication No. 2002-234830
Patent Document 3: Japanese Unexamined Patent Publication No. 2006-182746

SUMMARY OF INVENTION

Technical Problem

The main object of the present invention is to provide an externally applied composition capable of enhancing the stimulatory effect on IGF-1 secretion. Further, the present invention provides an externally applied composition capable of increasing the stratum corneum water content of the skin and maintaining the transepidermal water loss at an appropriate level.

Solution to Problem

As a result of intense research to achieve the above-described object, the inventors of the present invention found that an essential oil selected from the following group has an IGF-1 secretion stimulating effect, the group consisting of: star anise oil, cedar leaf oil, Atlas cedar oil, *Lavandula hybrida* oil, lime oil, peppermint oil, Scotch pine oil, rosemary oil, turpentine oil, ginger oil, cinnamon oil and clove oil. Further, based on this finding, the inventors discovered that the combination of an essential oil and a purine substance and/or a salt thereof can provide a superior stimulatory effect on IGF-1 secretion. In particular, when essential oils obtained from star anise, Scotch pine and *Lavandula hybrida* were combined, a significant stimulatory effect on IGF-1 secretion was confirmed. Further, the inventors of the present invention discovered that such a composition can increase the stratum corneum water content of the skin and maintain the transepidermal water loss at an appropriate level. Based on these findings, the inventors of the present invention conducted further research, and finally completed the present invention.

The present invention provides an externally applied composition as described below, a method of producing the externally applied composition and a method of stimulating IGF-1 secretion in the skin.

Item 1. An externally applied composition, comprising the following Component (A) and Component (B),
(A) at least one essential oil;
(B) at least one member selected from the group consisting of purine substances and salts thereof.
Item 2. The externally applied composition according to Item 1, wherein Component (A) is at least one essential oil selected from the group consisting of star anise oil, cedar leaf oil, Atlas cedar oil, *Lavandula hybrida* oil, lime oil, peppermint oil, Scotch pine oil, rosemary oil and turpentine oil.
Item 3. The externally applied composition according to Item 1 or 2, wherein Component (A) is at least one essential oil selected from the group consisting of star anise oil, Scotch pine oil and *Lavandula hybrida* oil.
Item 4. The externally applied composition according to any one of Items 1 through 3, wherein Component (A) is an essential oil comprising a mixture of star anise oil, Scotch pine oil and *Lavandula hybrida* oil.
Item 5. The externally applied composition according to any one of Items 1 through 4, wherein Component (A) is an essential oil comprising a mixture of star anise oil, cedar leaf oil, Atlas cedar oil, *Lavandula hybrida* oil, lime oil, peppermint oil, Scotch pine oil, rosemary oil and turpentine oil.
Item 6. The externally applied composition according to any one of Items 1 through 5, wherein Component (B) is adenosine phosphate or a salt thereof.
Item 7. The externally applied composition according to any one of Items 1 through 6, wherein Component (B) is adenosine-5'-monophosphate or a salt thereof.
Item 8. The externally applied composition according to any one of Items 1 through 7, wherein Component (A) is present in an amount of 0.00001 to 40 wt %.
Item 9. The externally applied composition according to any one of Items 1 through 8, wherein Component (B) is present in an amount of 0.01 to 20 wt %.
Item 10. The externally applied composition according to any one of Items 1 through 9, wherein Component (A) is present in an amount of 0.0000005 to 1,000 parts by weight per part by weight of Component (B).
Item 11. The externally applied composition according to any one of Items 1 through 10, wherein the composition is used to stimulate IGF-1 secretion in the skin.
Item 12. The externally applied composition according to any one of Items 1 through 10, wherein the composition is used to increase the stratum corneum water content of the skin.
Item 13. The externally applied composition according to any one of Items 1 through 10, wherein the composition is used to adjust the transepidermal water loss (TEWL) of the skin.
Item 14. The externally applied composition according to any one of Items 1 through 13, wherein the composition is in the form of a cosmetic composition or quasi-drug.
Item 15. A method of producing an externally applied composition for stimulating IGF-1 secretion, comprising combining the following Component (A) and Component (B),
(A) at least one essential oil;
(B) at least one member selected from the group consisting of purine substances and salts thereof.
Item 16. Use of the following Component (A) and Component (B) for producing an externally applied composition for stimulating IGF-1 secretion in the skin,
(A) at least one essential oil;
(B) at least one member selected from the group consisting of purine substances and salts thereof.
Item 17. A method of stimulating IGF-1 secretion in the skin, comprising applying the following Component (A) and Component (B) to the skin,
(A) at least one essential oil;
(B) at least one member selected from the group consisting of purine substances and salts thereof.
Item 18. A method of preventing/treating senile xerosis, comprising applying the following Component (A) and Component (B) to the skin,
(A) an essential oil;
(B) at least one member selected from the group consisting of purine substances and salts thereof.
Item 19. An externally applied composition, comprising a member of the capsaicin family and at least one member selected from the group consisting of purine substances and salts thereof.
Item 20. The externally applied composition according to Item 19, wherein the member of the capsaicin family is at least one member selected from the group consisting of capsaicin ((6E)-N-[(4-hydroxy-3-methoxyphenyl)methyl]-8-methylnon-6-enamide), nonyl acid vanillylamide (N-vanillylnonanamide) and dihydrocapsiate.

Advantageous Effects of Invention

The externally applied composition of the present invention combines an essential oil and a purine substance and/or a salt thereof, and thereby can synergistically enhance a stimulatory effect of the essential oil on IGF-1 growth and significantly stimulate IGF-1 secretion in the skin. The externally applied composition of the present invention has various effects such as: a reduction in pigmentation (reduction in the amount of melanin), an increase in skin brightness (prevention of dullness), stimulation of turnover, moisture retentivity of the skin and an increase in skin flexibility; and thus is capable of exhibiting skin anti-aging effects in an efficient and multifaceted manner.

Further, the externally applied composition of the present invention has an effect of increasing the stratum corneum water content and enhancing skin flexibility and elasticity. The externally applied composition of the present invention also has an effect of maintaining transepidermal water loss (TEWL) at an appropriate level. For example, aging in the skin is known to cause a reduction in transepidermal water loss, which dries the skin, and is accompanied by problems such as itching. Senile xerosis is a specific example of a disease that has the above-described symptoms. The composition of the present invention increases the stratum corneum water content and improves low TEWL, and thereby maintains skin moisture content at an appropriate level. This may create an effect of improving skin functions and the ability to maintain a youthful skin. Accordingly, the externally applied composition of the present invention may further be used for prevention/treatment of senile xerosis.

Itching, rashes and pimples may be caused when the stratum corneum water content is reduced, even if the transepidermal water loss is high. However, the externally applied composition of the present invention suppresses dryness of the skin and maintains the transepidermal water loss (TEWL) at an appropriate level, and is thus capable of preventing problems such as itching, rashes and pimples. As described above, the externally applied composition of the present invention can appropriately adjust the balance between the stratum corneum water content and transepidermal water loss, thus maintaining a normal skin condition and, further, a youthful skin. The term "adjust" used herein means to restore the skin to a healthy condition by improving low TEWL of the skin and/or by maintaining the TEWL level when the TEWL is at an appropriate level.

DESCRIPTION OF EMBODIMENTS

1. Externally Applied Composition

The externally applied composition on the skin of the present invention contains the following essential oil (hereinafter may be expressed as Component (A)) and a purine substance and/or a salt thereof (hereinafter may be expressed as Component (B)). The following describes the composition of the present invention in detail.

(A) Essential Oil

In the present invention, an essential oil used as Component (A) refers to an extracted liquid containing volatile and lipophilic aromatic substances from flowers, leaves/needles, fruits, roots, barks and other parts of plants. Preferably, it refers to an extracted liquid containing volatile and lipophilic aromatic substances from leaves/needles, fruits, roots, barks and other parts of plants.

The type of essential oil that may be used as Component (A) of the present invention is not particularly limited insofar as the effects of the present invention are not impaired, and essential oils obtained from various plant materials may be used. Essential oils include, for example, star anise (*Illicium verum*) oil, fennel (*Foeniculum vulgare*) oil, anise (*Pimpinella anisum*) oil, cedar leaf (*Thuja occidentalis* Linn.) oil, Atlas cedar (*Cedrus atlantica* Manetti) oil, *Lavandula hybrida* (*Lavandula hybrida*) oil, lime (*Citrus aurantifolia*) oil, peppermint (*Mentha arvensis* var. *piperascens*) oil, Scotch pine (*Pinus sylvestris*) oil, rosemary (*Rosmarinus officinalis* L.) oil, ginger (*Zingiber officinale*) oil, cinnamon (*Cinnamomum zeylanicum*) oil, clove oil (*Syzygium aromaticum*) oil and turpentine oil. Among these essential oils, star anise oil, fennel oil, anise oil, cedar leaf oil, Atlas cedar oil, *Lavandula hybrida* oil, lime oil, peppermint oil, Scotch pine oil, rosemary oil and turpentine oil are more preferable; star anise oil, fennel oil, anise oil, Scotch pine oil and *Lavandula hybrida* oil are even more preferable; and star anise oil, Scotch pine oil and *Lavandula hybrida* oil are particularly preferable.

The externally applied composition of the present invention may be formed of one member of the essential oils listed above, or an arbitrary combination of two or more of them. When using more than one essential oil, the form of the combination is not limited insofar as the effects of the present invention are not impaired. When using more than one essential oil, an example of a preferable combination in terms of the effects and aroma is a mixture of star anise oil, fennel oil, anise oil, cedar leaf oil, Atlas cedar oil, *Lavandula hybrida* oil, lime oil, peppermint oil, Scotch pine oil, rosemary oil and turpentine oil; and an example of a more preferable combination is a mixture of star anise oil, cedar leaf oil, Atlas cedar oil, *Lavandula hybrida* oil, lime oil, peppermint oil, Scotch pine oil, rosemary oil and turpentine oil.

In the present invention, the use of a mixture of essential oils or an essential oil containing a mixture as described above as Component (A) makes the effects of the present invention even more significant.

Insofar as a desired essential oil can be extracted, there are no limitations as to which part of various plant materials may be used for extraction of essential oils of the present invention. The parts that have been conventionally used may be used according to the types of plants. Preferable plant parts include the flowers, stems, leaves/needles, branches, fruits and roots of various plants; and aerial parts of the plants. Further preferable plant parts include stems, leaves/needles, branches, fruits and roots of various plants; and aerial parts of the plants. In addition, each part of the plant may be used in a suitable combination. More specifically, regarding star anise oil, fennel oil and anise oil, essential oils thereof are preferably extracted from the fruits (or dried fruits). Cedar leaf oil is preferably extracted from the foliage. Atlas cedar oil is preferably extracted from the bark. *Lavandula hybrida* oil is preferably extracted from the whole plant. Lime oil is preferably extracted from the fruit and fruit peels. Peppermint oil is preferably extracted from the whole plant. Scotch pine oil is preferably extracted from the needles. Rosemary oil is preferably extracted from the leaves. Turpentine oil is preferably extracted from Pinaceae trees.

Essential oils used in the present invention may be extracted according to a conventionally known method. Common extraction methods include steam distillation, enfleurage, solvent extraction and expression. These essential oil extraction methods may be suitably selected based on the type and extraction parts of plant materials to be used and the nature of the extracted essential oils. Additionally, for more convenience, various commercially available essential oils may be purchased and used. Various essential oils are available from, for example, Koshiro Company Limited, Shiseido Seiyaku Kabushiki Kaisha (Shiseido Pharmaceutical Co., Ltd.) and K.K. Eikodo Honten.

The percentage of Component (A) in the externally applied composition of the present invention is not particularly limited insofar as the effects of the present invention are not impaired. However, the percentage of the total weight of Component (A) is, for example, not less than 0.00001 wt %, preferably 0.00001 to 40 wt %, more preferably 0.0001 to 30 wt %, and further preferably 0.0001 to 25 wt %.

(B) Purine Substance And Salt Thereof

Component (B) used in the externally applied composition of the present invention is at least one member selected from the group consisting of purine substances and salts thereof. In the present invention, a "purine substance" denotes one of various derivatives having a purine or a purine nucleus as a skeleton (hereinafter referred to as a purine substance).

The purine substances usable in the present invention are not particularly limited. Examples of purine substances include adenine, guanine, hypoxanthine, xanthine, adenosine, guanosine, inosine, adenosine phosphates [adenosine 2'-monophosphate, adenosine 3'-monophosphate, adenosine 5'-monophosphate (AMP), cyclic adenosine 3'5'-monophosphate (cAMP), adenosine 5'-diphosphate (ADP), adenosine 5'-triphosphate (ATP)], guanosine phosphates (guanosine 3'-monophosphate, guanosine 5'-monophosphate, guanosine 5'-diphosphate, guanosine 5'-triphosphate), adenylosuccinic acid, xanthylic acid, inosinic acid, flavine adenine dinucleotide (FAD) and nicotinamide adenine dinucleotide (NAD). Preferable among these are adenosine monophosphates (adenosine 2'-monophosphate, adenosine 3'-monophosphate, AMP and cAMP). In particular, the use of AMP in combination with the Component (A) can make the stimulatory effect on IGF-1 secretion even more significant, increase the stratum corneum water content and maintain the transepidermal water loss at a further appropriate level. Thus, AMP is preferred as Component (B).

The purine substance salts usable in the present invention are also not particularly limited. Examples of such purine substance salts include alkali metal salts such as sodium salts and potassium salts; alkaline earth metal salts such as calcium salts, magnesium salts and barium salts; salts of basic amino acids such as arginine and lysine; salts of ammoniums such as ammonium, tricyclohexylammonium salts; salts of alkanolamines such as monoisopropanolamine, diisopropanolamine and triisopropanolamine; and aliphatic dihydric alcohol derivatives such as aminomethyl propanol, aminomethyl propanediol and aminohydroxymethyl propanediol. Alkali metal salts of purine substances are particularly preferred.

Particularly suitable substances to be used as Component (B) in the present invention are adenosine monophosphate monosodium and adenosine monophosphate disodium.

Component (B) in the externally applied composition of the present invention may be formed of one member of the substances above, or an arbitrary combination of two or more of them. When using more than one kind, the form of the combination is not limited insofar as the effects of the present invention are not impaired.

The percentage of the total weight of Component (B) with respect to the total weight of the externally applied composition of the present invention is, for example, not less than 0.01 wt %, preferably 0.1 to 20 wt %, and further preferably 0.1 to 10 wt %. When Component (B) is a salt of a purine substance, the percentage is converted to the weight of the purine substance.

Insofar as the externally applied composition of the present invention contains both Component (A) and Component (B), there are no limitations as to the form of the combination of the two components. Preferable examples of the combination of Component (A) (an essential oil) and Component (B) (a purine substance and/or a salt thereof) for the externally applied composition of the present invention include: a combination of a mixture of star anise oil, fennel oil, anise oil, cedar leaf oil, Atlas cedar (bark) oil, *Lavandula hybrida* oil, lime oil, peppermint oil, Scotch pine (needle) oil, rosemary oil and turpentine oil as Component (A), and adenosine phosphate or a salt thereof as Component (B); a combination of an essential oil comprising at least one member selected from the group consisting of star anise oil, fennel oil, anise oil, Scotch pine oil and *Lavandula hybrida* oil as Component (A), and AMP or a salt thereof as Component (B); and a combination of star anise oil, cedar leaf oil, Atlas cedar oil, *Lavandula hybrida* oil, lime oil, peppermint oil, Scotch pine oil, rosemary oil and turpentine oil as Component (A), and AMP or a salt thereof as Component (B). These combinations of Component (A) and Component (B) make the superior effects of the present invention even more significant.

The ratio of Component (A) and Component (B) in the externally applied composition of the present invention is not particularly limited, and is suitably set according to the aforementioned percentages of Component (A) and Component (B), the form of the composition, the desired effects and other factors. For one suitable mixture, the ratio range of the total weight of Component (A) is 0.0000005 to 1,000 parts by weight, preferably 0.000005 to 100 parts by weight, more preferably 0.000001 to 100 parts by weight, and further preferably 0.0001 to 100 parts by weight per part by weight of Component (B). When Component (B) is a salt of a purine substance, the ratio is converted to the weight of the purine substance.

(C) Other Components

The externally applied composition of the present invention usually has a pH ranging from that of a weak acid to that of a neutral substance. With a view to minimizing irritation of the skin and alleviating pigmentation, the composition preferably has a pH in the range of 5 to 7, and more preferably 5.5 to 7. pH adjusters may be incorporated into the externally applied composition on the skin of the present invention so as to control the pH within the above range. Such pH adjusters are not limited insofar as they are weakly alkaline or alkaline and pharmacologically or cosmetically acceptable. Examples of pH adjusters include sodium hydroxide, L-arginine, aminomethylpropanediol, diisopropanolamine and triethanolamine.

In addition to the above components, the externally applied composition of the present invention may contain, as required, a variety of components or additives that are generally incorporated into externally applied preparations. Examples of such components include surfactants, solubilizers, fats or oils, polyhydric alcohols, viscosity improvers, antiseptics, bactericides, humectants, colorants, dispersants, antioxidants, sequestering agents, astringents, whiteners, pigments, deodorizers and flavors. Such components may be used singly or in any combination of two or more members.

The externally applied composition of the present invention may take any form insofar as it is formulated as a composition externally applied to the skin. For example, the externally applied composition of the present invention may be produced as external preparations in desirable forms such as pastes, mousses, gels, liquids, emulsions, suspensions, creams, ointments, sheets, sticks, aerosol formulations, spray formulations and liniments by combining the above-mentioned components, as required, into the externally applied composition of the invention, and further adding other solvents or conventionally used bases or carriers for external preparations into the composition as required. Such formulations can be prepared using general techniques in this field.

The usage of the externally applied composition of the present invention is also not particularly limited. For example, the externally applied composition of the present invention can be adopted as various external preparations, such as externally applied drugs for the skin; externally applied quasi-drugs for the skin; makeup cosmetics such as foundations, blushes, lipsticks, mascaras, eye shadows, eyeliners, face powders and sunscreens; basic skin care products such as emulsions, creams, lotions, oils and packs; washes such as facial washes, cleansing creams and body washes; cleaning agents; cleaners; and bath agents.

The externally applied composition of the present invention is used by being applied to human skin. The amount and frequency of application of the externally applied composition of the present invention are not particularly limited. For example, the composition may be applied to the skin of the entire body (particularly in areas with problematic pigmentation (blemishes), wrinkles, dryness (for example, on the elbows, knees and heels), itching, rashes and pimples) in a suitable amount once or several times per day, according to the types and/or concentrations of the active ingredients used, the age/sex of the user, the condition of the problem part of the skin, the application method, the expected intention and other factors. Insofar as the externally applied composition of the present invention is applicable to the skin, there are no limitations as to what body parts the composition should be applicable to; the composition is applicable to the entire body.

As shown in the following experimental examples, the externally applied composition of the present invention has a stimulatory effect on IGF-1 secretion in the skin. IGF-1 (insulin-like growth factor-1) is a polypeptide highly similar in sequence to insulin. In addition to an insulin-like effect (hypoglycemic action), IGF-1 has a stimulatory effect on cell growth, and adjusts cell DNA synthesis. Accordingly, as IGF-1 secretion in the skin is stimulated, skin cell growth is stimulated, which improves the diseases and symptoms of the epithelial layer of the skin, thereby allowing a healthy condition of the skin to be maintained.

As described above, the externally applied composition of the present invention may be used as an externally applied composition for stimulating IGF-1 secretion, or a composition for stimulating IGF-1 growth. Further, based on the function to stimulate IGF-1 secretion, the externally applied composition of the present invention more efficiently ensures the following effects: moisture retentivity of the skin, increase in skin flexibility, reduction of pigmentation (reduction in the amount of melanin), diminishment of chloasma, increase in skin brightness (prevention of dullness) and a turnover-stimulating effect. Accordingly, the externally applied composition of the present invention is useful as a skin anti-aging composition, a moisturizing composition, a composition for alleviating pigmentation, or a whitening composition.

In addition, the externally applied composition of the present invention has an effect of increasing the stratum corneum water content and softening the stratum corneum. Accordingly, the externally applied composition of the present invention may be used as an externally applied composition for increasing the stratum corneum water content of the skin. An increase in the stratum corneum water content can be measured by a conventionally known method. For example, SKICON-200 (manufactured by IBS Co., Ltd.) or other measuring devices can be used. With a device as described above, a change in the stratum corneum water content can be evaluated using electrical conductance (μS) as an index.

Further, the externally applied composition of the present invention also has an effect of appropriately maintaining transepidermal water loss. Transepidermal water loss indicates the amount of water that passes from inside the body through the skin to the outside of the body. Maintaining transepidential water loss at an appropriate level can lead to the suppression of dryness of the skin and the prevention of problems such as itching, rashes and pimples. The externally applied composition of the present invention can not only improve the stratum corneum water content, but also appropriately maintain the transepidermal water loss, and is thus capable of maintaining a normal skin condition and achieving a more youthful skin. In other words, when the externally applied composition of the present invention is applied to skin having low transepidermal water loss (TEWL), the composition can increase and maintain the TEWL at an appropriate level. In addition, when the TEWL is at an appropriate level, application of the externally applied composition of the present invention to the skin can help to maintain the level, thereby restoring the skin to a healthy condition. Accordingly, the externally applied composition of the present invention may be used as an externally applied composition for increasing or adjusting the transepidermal water loss. Note that the transepidermal water loss can be measured according to a conventionally known method. For example, DermaLab (manufactured by Cortex Technology) may be used.

As described above, the externally applied composition of the present invention may also be used as an externally applied composition for achieving an appropriate level of transepidermal water loss while maintaining a high stratum corneum water content. In addition, the above-described functions of the externally applied composition of the present invention are effective in improving stratum corneum functions, and thus the healthy condition of the stratum corneum can be maintained. Further, the externally applied composition of the present invention is effective in improving symptoms of aged skin having a low stratum corneum water content and transepidermal water loss (specifically, symptoms such as coarseness of the skin surface, light chapping and itching), and is also effectively applicable for the prevention/treatment of diseases specifically caused by stratum corneum with a reduced water-holding ability and barrier function (for example, senile xerosis).

Further, the present invention provides a method of stimulating IGF-1 secretion in the skin, comprising applying the Component (A) and the Component (B) to the skin. The present invention also provides a method of preventing/treating senile xerosis based on the improved effect of water-holding function of the skin achieved by stimulating IGF-1 secretion. An amount of application of each component in these methods is set according to the degree and range of symptoms. For example, the amount of the Component (B) is preferably 1 to 5,000 mg/day in a dosage divided into two to three dosages a day.

The present invention also provides a method of easily producing the externally applied composition having a stimulatory effect on IGF-1 secretion by combining another component with the Components (A) and (B) as required. Specific examples of each component, the amount of the components, and the like in the production method of the present invention are as described above.

2. Composition of Different Combination

The inventors of the present invention further discovered that the use of a member of the capsaicin family in combination with a purine substance and/or a salt thereof (Component (B)) stimulates IGF-1 secretion, as shown by the examples below. Accordingly, the present invention also provides an externally applied composition containing the above Component (B) and a member of the capsaicin family. Note that, unlike essential oils characterized by their aroma and volatility, members of the capsaicin family used herein exhibit no aroma or volatility, and thus are not regarded as essential oils, and are distinguished therefrom.

Members of the capsaicin family are known as the spicy components in chili peppers. Such members include capsaicinoids (a collective term for compounds having fatty acids attached to vanillylamine by acid amino bonding) and capsinoids (a collective term for compounds having fatty acids attached to alcohol by ester bonding). Capsaicinoid includes, for example, capsaicin ((6E)-N-[(4-hydroxy-3-methoxyphenyl)methyl]-8-methylnon-6-enamide) and nonyl acid vanillylamide (N-vanillylnonanamide), i.e., a synthetic capsaicinoid. Capsinoids include, for example, dihydrocapsiate. In the present invention, capsaicin and synthetic capsaicinoid are preferably used. Capsaicin may be used by extraction according to a conventionally known method, using a chili pepper as a raw material. Alternatively, for more convenience, commercially available capsaicin may be purchased from a company such as Tokyo Chemical Industry Co., Ltd.

The percentage of the weight of the member of the capsaicin family with respect to the total weight of the externally applied composition of the present invention is, for example, not less than 0.000001 wt %, preferably 0.000001 to 0.01 wt %, and further preferably 0.000001 to 0.005 wt %.

The above-described purine substance and/or salt thereof may be used as Component (B).

The ratio between Component (B) and the member of the capsaicin family in the externally applied composition of the present invention is not particularly limited insofar as the effects of the present invention are not impaired. For one suitable mixture, the ratio of the member of the capsaicin family is 0.00000005 to 1 part by weight, preferably 0.00000005 to 0.1 parts by weight, and further preferably 0.0000001 to 0.1 parts by weight per part by weight of Component (B). When Component (B) is a salt of a purine substance, the ratio is converted to the weight of the purine substance.

Forms and application methods of the externally applied composition containing Component (B) and a member of the capsaicin family are also as described above in "1. Externally applied composition".

Members of the capsaicin family have been known as IGF-1 secretion stimulants. The present invention uses a member of the capsaicin family and a purine substance in combination, and thereby achieves an increased IGF-1 secretion stimulation compared to when a member of the capsaicin family is used alone. In addition, the concentration of a member of the capsaicin family can be reduced by using the member of the capsaicin family in combination with a purine substance.

EXAMPLES

The present invention is more specifically explained with reference to the Experimental Examples Experiment, etc. However, the present invention is not limited to the Examples. Note that the symbol "%" indicates "wt %" in the following examples, comparative examples and reference example, unless otherwise specified.

Examples 1 to 3 and Comparative Examples 1 to 5

In order to examine how the effect of essential oils on the amount of IGF-1 secretion in the skin is affected by AMP, the following compositions containing an essential oil and AMP (Examples 1 to 3 and Comparative Examples 1 to 5) were prepared by a standard method. The pH of each composition was adjusted with NaOH such that the pH ranged from 6.5 to 7.0.

TABLE 1

| | | Anhydrous ethanol | PEN 4630 | AMP | Star anise oil | Scotch pine needle oil | *Lavandula hybrida* oil | Phosphate buffer solution (pH 7.0) | NaOH |
|---|---|---|---|---|---|---|---|---|---|
| Example 1 | 20% Star anise oil + 10% AMP | 20 | 1 | 10 | 20 | — | — | remainder | Suitable amount |
| Example 2 | 20% Scotch pine needle Oil + 10% AMP | 20 | 1 | 10 | — | 20 | — | remainder | Suitable amount |
| Example 3 | 20% *Lavandula hybrida* oil + 10% AMP | 20 | 1 | 10 | — | — | 20 | remainder | Suitable amount |
| Comparative Example 1 | Base | 20 | 1 | — | — | — | — | remainder | Suitable amount |
| Comparative Example 2 | 10% AMP | 20 | 1 | 10 | — | — | — | remainder | Suitable amount |
| Comparative Example 3 | 20% Star anise oil | 20 | 1 | — | 20 | — | — | remainder | Suitable amount |
| Comparative Example 4 | 20% Scotch pine needle oil | 20 | 1 | — | — | 20 | — | remainder | Suitable amount |
| Comparative Example 5 | 20% *Lavandula hybrida* oil | 20 | 1 | — | — | — | 20 | remainder | Suitable amount |

PEN 4630: polyoxyethylene polyoxypropylene decyltetradecyl ether
AMP: adenosine-5'-monophosphate
Star anise oil: essential oil derived from the fruit of star anise (manufactured by K.K. Eikodo Honten)
Scotch pine needle oil: essential oil derived from the needles of Scotch pine (manufactured by K.K. Eikodo Honten)
*Lavandula hybrida* oil: essential oil derived from the whole plant of *Lavandula hybrida* (manufactured by K.K. Eikodo Honten)
Phosphate buffer solution: phosphate buffer powder (1/15 mol/l, ph 7.0; manufactured by Wako Pure Chemical Industries, Ltd.)

Experimental Example 1: Effect of Combination of Essential Oil and AMP on IGF-1 Secretion Stimulation (1)

Experiment 1-1

400 μl of a test solution was applied to the skin on the back (3 cm×5 cm) of hairless mice (Hos: HR-1, Japan SLC, Inc., female, 6 to 8 weeks age). 30 minutes after the application, the skin was extracted and frozen-crushed. Then, the IGF-1 concentration in the skin was measured using Quantikine (registered trademark) Mouse IGF-1 Immunoassay (R&D Systems, Inc.).

The study groups were as shown in Table 2 below. The composition shown in Table 1 was used as a test solution. FIG. 1a shows the results (average value±standard error).

TABLE 2

| Study Group | Number of mice |
|---|---|
| Non-administration | 6 |
| Comparative Example 2 (10% AMP) | 6 |
| Comparative Example 3 (20% star anise oil) | 6 |
| Example 1 (20% star anise oil + 10% AMP) | 6 |

Experiment 1-2

The secreted IGF-1 concentration was measured according to the method described in Experiment 1-1. The study groups were as shown in Table 3 below. The composition shown in Table 1 above was used as a test solution. FIG. 1b shows the results (average value±standard error).

TABLE 3

| Study Group | Number of mice |
|---|---|
| Comparative Example 1 (base) | 6 |
| Comparative Example 2 (10% AMP) | 6 |
| Comparative Example 4 (20% Scotch pine needle oil) | 6 |
| Example 2 (20% Scotch pine needle oil + 10% AMP) | 6 |

Experiment 1-3

The secreted IGF-1 concentration was measured according to the method described in Experiment 1-1. The study groups were as shown in Table 4 below. The composition shown in Table 1 above was used as a test solution. FIG. 1c shows the results (average value±standard error).

TABLE 4

| Study Group | Number of mice |
|---|---|
| Comparative Example 1 (base) | 6 |
| Comparative Example 2 (10% AMP) | 6 |
| Comparative Example 5 (20% *Lavandula hybrida* oil) | 6 |
| Example 3 (20% *Lavandula hybrida* + 10% AMP) | 6 |

According to the results in FIG. 1a (star anise oil+AMP), star anise oil itself showed a stimulatory effect on IGF-1 secretion in the skin. Although AMP did not produce a stimulatory effect on IGF-1 secretion when used alone, the results show that the use of AMP in combination with star anise oil significantly enhanced the stimulatory effect (P=0.0002, 1-Way ANOVA).

According to the results in FIG. 1b (Scotch pine oil+ AMP), neither AMP or Scotch pine needle oil stimulated IGF-1 secretion when used alone; however, the use of AMP in combination with Scotch pine oil significantly enhanced the IGF-1 secretion (P=0.0175, 1-Way ANOVA).

According to the results in FIG. 1c (*Lavandula hybrida* oil+AMP), a tendency of a significant enhancement in the IGF-1 secretion was shown when *Lavandula hybrida* oil was used in combination with AMP.

The above results show that the use of AMP alone did not produce a sufficient stimulatory effect on IGF-1 secretion; however, the compositions of Examples 1, 2 and 3, particularly Examples 1 and 2, showed a significant stimulatory effect on IGF-1 secretion.

Star anise oil is known to contain anethole as a main component. Anethole is also contained in oils such as fennel oil and anise oil. Thus, an excellent stimulatory effect on IGF-1 secretion can be expected from the combination of fennel oil and anise oil with AMP, similar to when the star anise oil is combined with AMP.

Experimental Example 2: Effect of Combination of Nonyl Acid Vanillylamide and AMP on IGF-1 Secretion Stimulation A test solution was prepared in the same manner as described in Experimental Example 1 using nonyl acid vanillylamide (manufactured by Tokyo Chemical Industry Co., Ltd.); concentration: 0.001%) instead of the essential oils shown in Table 1 above. This solution was used as Reference Example 1. In addition, a test solution formed without adding nonyl acid vanillylamide to Reference Example 1 (referred to as Comparative Example 6), and a test solution formed without adding AMP to Reference Example 1 (referred to as Comparative Example 7) were used as comparisons.

400 μl of a test solution was applied to the skin on the back (3 cm×5 cm) of hairless mice (Hos: HR-1, Japan SLC, Inc., female, 6 to 8 weeks age). 60 minutes after the application, the skin was extracted and frozen-crushed. Then, the IGF-1 concentration in the skin was measured using Quantikine (registered trademark) Mouse IGF-1 Immunoassay (R&D Systems, Inc.). The study groups were as shown in Table 5 below. FIG. 2 shows the results. The value of IGF-1 concentration indicates a mean value (n=3).

TABLE 5

| Study Group | Number of mice |
|---|---|
| Comparative Example 1 (base) | 3 |
| Comparative Example 6 (1% AMP) | 3 |
| Comparative Example 7 (0.001% nonyl acid vanillylamide) | 3 |
| Reference Example 1 (0.001% nonyl acid vanillylamide + 1% AMP) | 3 |

According to FIG. 2, the use of nonyl acid vanillylamide in combination with AMP also showed a stimulatory effect on IGF-1 secretion.

Experimental Example 3: Effect of Combination of Essential Oil and AMP on IGF-1 Secretion Stimulation (2)

300 μl of a test solution was applied to the skin on the back (3 cm×5 cm) of hairless mice (Hos: HR-1, Japan SLC, Inc., female, 7 weeks age). 30 minutes after the application, the skin was extracted and frozen-crushed. Then, the IGF-1 concentration in the skin was measured using Quantikine (registered trademark) Mouse IGF-1 Immunoassay (R&D Systems, Inc.).

This experiment was a comparison between the two groups: one with application and one without application. A composition used as the test solution included: 0.03% of an essential oil mixture in which star anise oil, Scotch pine oil and *Lavandula hybrida* oil (these oils were confirmed to have a stimulatory effect on IGF-1 secretion in Experimental Example 1) were combined with other essential oils (Atlas cedar oil, cedar leaf oil, lime oil, peppermint oil, rosemary oil and turpentine oil) for desired aroma effects; 1% of AMP;

and a milk formulation supplemented with appropriate common materials. Table 6 shows the results (average value±standard error).

TABLE 6

|  | Amount of IGF-1 (ng/g tissue) |
|---|---|
| Control (Non-application) (n = 6) | 72.3 ± 2.3 |
| Test solution application (n = 6) | 85.1 ± 2.9 |

Table 6 shows that a formulation in which an essential oil mixture was combined with an AMP also produced a significant stimulatory effect on IGF-1 secretion (P<0.05).

Additionally, as described above, when a total of nine oils including star anise oil, Scotch pine oil, *Lavandula hybrida* oil and other essential oils mentioned above were mixed together, it produced a particularly superior property in terms of aroma.

Experimental Example 4: Effects on the Stratum Corneum Water Content and Transepidermal Water Loss (1)

This experimental example was performed with 9 healthy men aged 30 to 55 years (averaged 45 years), who served as subjects. Areas of 5×8 cm were marked on the left and right front thighs of each subject, and used as test sites. The test solution was applied to one of the left or right test sites, and the other test site was left without application. The amount of application was approximately 0.1 g (which corresponds to 2 drops from the container that was used) per time, two times a day (morning and evening). The test solution was applied during a period from 6:00 to 12:00 in the morning and a period from 18:00 to 24:00 in the evening, after bathing. The test solution used was skin milk moisturizer having the composition as shown in Table 7 below.

TABLE 7

|  | Components | Amount of Components (wt %) |
|---|---|---|
| 1 | Adenosine monophosphate | 1.0 |
| 2 | Monoisostearic acid polyglyceryl | 2.0 |
| 3 | Monomyristic acid decaglyceryl | 0.5 |
| 4 | Tri-2-ethylhexane acid glyceryl | 1.0 |
| 5 | Liquid paraffin | 4.0 |
| 6 | Acetic acid-dl-α-tocophenol | 0.1 |
| 7 | Concentrated glycerin | 3.0 |
| 8 | Dipropylene glycol | 3.0 |
| 9 | Acrylic acid-methacrylic acid alkyl copolymer | 0.4 |
| 10 | Essential oil mixture*[1] | 0.05 |
| 11 | Preservatives | Suitable amount |
| 12 | pH adjuster | Suitable amount |
| 13 | Purified water | Remainder |

*[1]Essential oil mixture: a mixture of essential oils derived from star anise, cedar leaf, Atlas cedar, *Lavandula hybrida*, lime, peppermint, Scotch pine, rosemary and turpentine.

The subjects washed the test sites (thigh) using a specified type of soap (Kao White, manufactured by Kao Corporation), marked the test site using an oil-based pen, and then rested in bed for about 20 minutes on their backs, in a room where the temperature was controlled at 20° C. and the relative humidity at 50% RH. Subsequently, the stratum corneum water content and transepidermal water loss were measured. At this time, the non-application site was used as a control. The measurement was performed before the start of application and after the fourth and eighth weeks of application. FIGS. 3a and 3b show the results.

The measurement of the stratum corneum water content and transepidermal water loss and data analysis were performed according to the following methods.

Stratum Corneum Water Content

Electrical conductance (μS) was measured using SKICON-200 (IBS Co., Ltd), which was used as an index of the stratum corneum water content. The measurements were repeated 7 times, and the average of 5 measurement values on the median was used as the measured value.

Transepidermal Water Loss (TEWL)

The transepidermal water loss (g/h-m$^2$) was measured using DermaLab (Cortex Technology). The measurements were repeated 5 times, and the average of the measurements was used as the measured value.

Data Analysis

A t-test was used to compare the pairs of values on each measurement day (after the fourth and eighth weeks of application) in order to determine the significance of difference between the control group and the application group. In the figures, # indicates a significant difference (P<0.05).

The results in FIG. 3a show that the stratum corneum water content significantly increased after four weeks and eight weeks of application of the test solution. Additionally, FIG. 3b shows a significant rise in the TEWL after the eighth week of application of the externally applied composition of the present invention, compared to the control group.

In other words, the results show that the application of the test solution helped to maintain both the stratum corneum water content and transepidermal water loss at high levels simultaneously, resulting in the maintenance of a healthy skin condition.

Further, in Experimental Example 4, the effects of the test solution were evaluated in terms of the flexibility and elasticity, which are common indices of effects on the skin. FIGS. 3c and 3d show the evaluated results.

The measurements of the flexibility and elasticity and data analysis were performed according to the following methods.

Flexibility And Elasticity

The flexibility and elasticity were measured using Cutometer MPA580 (CK electronic GmbH). The measurement was performed according to a standard method described in the instruction manuals provided with the equipment. The measurements were repeated 5 times, and the average of the measurement values was used as the measured value.

Data Analysis

A t-test was used to compare the pairs of values on each measurement day (after the fourth and eighth weeks of application) in order to determine significance of difference between the control group and the application group. In the figure, # indicates a significant difference (P<0.05).

The result in FIG. 3c shows that application of the test solution significantly suppressed a reduction in skin flexibility. Additionally, FIG. 3d shows a rise in skin elasticity.

Further, images of skin samples were taken before and after the application of the test solution in order to confirm a change in the skin surface texture caused by the application.

Evaluation of Skin Surface Texture

Evaluation of the skin surface texture was performed by producing skin samples. For the skin samples, a reflection-type skin replica analysis system ASA-03R (AsahiBiomed Co., Ltd.) was used to create a replica of forms of the skin surface according to a method described in the instruction manuals provided with the equipment, and images thereof were taken for evaluation.

The results in FIG. 3e show that application of the test solution for eight weeks clearly made the skin texture finer.

The results of Experimental Example 4 show that application of a combination of AMP and the mixture of the above described nine essential oils to the skin helped to maintain the normal water content of the skin, and further to improve the flexibility and elasticity. In addition, when the externally applied composition of the present invention was applied to the skin, the composition made the skin surface texture finer, creating a fresh-looking and healthy skin.

Experimental Example 5: Effects on the Stratum Corneum Water Content and Transepidermal Water Loss (2)

The following experiments were performed in order to confirm that these effects are obtainable on the entire body. This experimental example was performed with 7 healthy men aged 39 to 57 years (average 49.0 years), who served as subjects. An area of 4×4 cm was marked on one of the left or right heels of each subject, and used as a test site. The test solution (cream formulation containing 0.5% AMP and 0.03% essential oil mixture) was applied to the other test site was left without application. The amount of application was approximately 0.2 g per time, two times a day (morning and evening). The test solution was applied during a period from 6:00 to 12:00 in the morning and a period from 18:00 to 24:00 in the evening, after bathing.

Subsequently, in the same manner as in Experimental Example 4, the subjects underwent the measurement of the stratum corneum water content and transepidermal water loss, and images of the test sites were taken. The measurement was performed before the start of application and after the fourth and eighth weeks of application. FIG. 4 shows the results.

FIGS. 4a and 4b show an apparent increase in the stratum corneum water content and a significant rise in the TEWL by the application of the test solution, compared to the non-application test site.

Further, the test site to be evaluated was photographed eight weeks after the start of the experiment, and enlarged images thereof were developed in order to confirm the effects of the application of the test solution on the skin. FIG. 4c shows the images.

The results in FIG. 4c clearly show that the condition of the skin surface was improved as a result of the application of the test solution.

Among the portions of the body surface, the heel portion is commonly particularly prone to problems such as dryness and chapping. However, this experimental example showed an increase in the stratum corneum water content, a rise in the transepidermal water loss and an apparent improvement in the condition of the skin surface of the heel portion.

Experimental Example 6: Effects on the Stratum Corneum Water Content and Transepidermal Water Loss (3)

This experimental example was performed with 5 healthy men aged 47 to 57 years (averaged 53.2 years), who served as subjects. Areas of 4×4 cm were marked at two locations (elbow side and wrist side) on each of the left and right inside forearms of each subject, and used as test sites. A test solution (the skin milk moisturizer used in the above Experimental Example 3) was applied to the elbow-side test site on either one of the left or right forearms. A general, commercially available skin milk moisturizer (a commercial formulation) containing neither adenosine monophosphate nor essential oils was applied to the other elbow-side test site. The number of applications was two times a day (morning and evening). The test solution was applied during a period from 6:00 to 12:00 in the morning and a period from 18:00 to 24:00 in the evening, after bathing. The amount of application was approximately 0.05 g (which corresponds to 1 drop from the container that was used) per time.

The subjects washed the test sites (inside forearm) using a specified type of soap (Kao White, manufactured by Kao Corporation), marked the test sites using an oil-based pen, and then rested in bed for about 20 minutes on their backs, in a room where the temperature was controlled at 20° C. and the relative humidity at 50% RH. Subsequently, the stratum corneum water content and transepidermal water loss (TEWL) were measured. The measurement was performed before the start of application and at the fourth week of application.

The measurement of the stratum corneum water content and transepidermal water loss and data analysis were performed by the same method as in Experimental Example 4. FIGS. 5a and 5b show the results.

FIGS. 5a and 5b show that the stratum corneum water content increased in both cases where the test solution was applied and where the commercial formulation was applied. The TEWL level showed a significant rise after the fourth week on the test site where the test solution was applied, compared to the test site where the commercial formulation was applied.

In other words, the results show that the application of the test solution helped to achieve a high stratum corneum water content and high transepidermal water loss simultaneously, resulting in the maintenance of the youthful and healthy condition of the skin. When general skin milk moisturizer was applied, only the stratum corneum water content was maintained at a high level, and the level of transepidermal water loss did not improve.

In addition, a similar experiment was performed for another test solution (skin lotion) and a comparison was made with a commercial formulation (skin lotion). An increase in the stratum corneum water content was found in both cases; however, the TEWL tended to rise when the test solution (the skin lotion) was used. The skin lotion used as the test solution has the following composition.

TABLE 8

| | Components | Amount of Components (wt %) |
|---|---|---|
| 1 | Adenosine monophosphate | 1.0 |
| 2 | 1,3-butylene glycol | 2.0 |
| 3 | Concentrated glycerin | 2.0 |
| 4 | Monolauric acid polyoxyethylene sorbitan (20 E.O.) | 1.0 |
| 5 | Ethanol | 5.0 |
| 6 | Essential oil mixture*[1] | 0.05 |
| 7 | Preservatives | Suitable amount |
| 8 | pH adjuster | Suitable amount |
| 9 | Purified water | Remainder |

*[1]The same essential oil mixture as in Table 7 was used.

Formulation Examples

Formulation examples of the externally applied composition of the present invention are shown below. However, the present invention is not limited to those examples. Lotions, emulsions and serums may be formulated, by conventional methods, based on the compositions listed in the formulation examples. Note that the total amount of each formulation example is expressed as 100% by weight.

TABLE 9

Lotion

| | Components | Amount of Components (wt %) |
|---|---|---|
| 1 | Adenosine-5'-monophosphate disodium | 2.0 |
| 2 | 1,3-butylene glycol | 2.0 |
| 3 | Concentrated glycerin | 2.0 |
| 4 | Monolauric acid polyoxyethylene sorbitan | 1.0 |
| 5 | Ethanol | 5.0 |
| 6 | Star anise oil | 0.02 |
| 7 | Preservatives | Suitable amount |
| 8 | pH adjuster | Suitable amount |
| 9 | Purified water | Remainder |

TABLE 10

Emulsion

| | Components | Amount of Components (wt %) |
|---|---|---|
| 1 | Adenosine 3',5'-cyclic phosphoric acid | 0.5 |
| 2 | Monostearic acid decaglyceryl | 2.0 |
| 3 | Monostearic acid glyceryl | 1.0 |
| 4 | Stearic acid | 3.0 |
| 5 | Behenyl alcohol | 2.0 |
| 6 | Tri-2-ethylhexane acid glyceryl | 5.0 |
| 7 | Squalane | 2.0 |
| 8 | Decamethylcyclopentasiloxane | 1.0 |
| 9 | Acetic acid-dl-α-tocophenol | 0.1 |
| 10 | Concentrated glycerin | 2.0 |
| 11 | 1,3-butylene glycol | 3.0 |
| 12 | Acrylic acid-methacrylic acid alkyl copolymer | 0.1 |
| 13 | Essential oil mixture*[1] | 0.1 |
| 14 | Preservatives | Suitable amount |
| 15 | pH adjuster | Suitable amount |
| 16 | Purified water | Remainder |

*[1]The same essential oil mixture as in Table 7 was used.

TABLE 11

Serum

| | Components | Amount of Components (wt %) |
|---|---|---|
| 1 | Adenosine triphosphate disodium | 1.0 |
| 2 | Dipropylene glycol | 3.0 |
| 3 | Concentrated glycerin | 2.0 |
| 4 | Sodium hyaluronate | 0.1 |
| 5 | Polyoxyethylene-methylpolysiloxane copolymer | 0.5 |
| 6 | Methoxyethylene-maleic anhydride copolymer | 0.2 |
| 7 | Ethanol | 3.0 |
| 8 | *Lavandula hybrida* oil | 0.05 |
| 9 | Preservatives | Suitable amount |
| 10 | pH adjuster | Suitable amount |
| 11 | Purified water | Remainder |

Figure 1A:
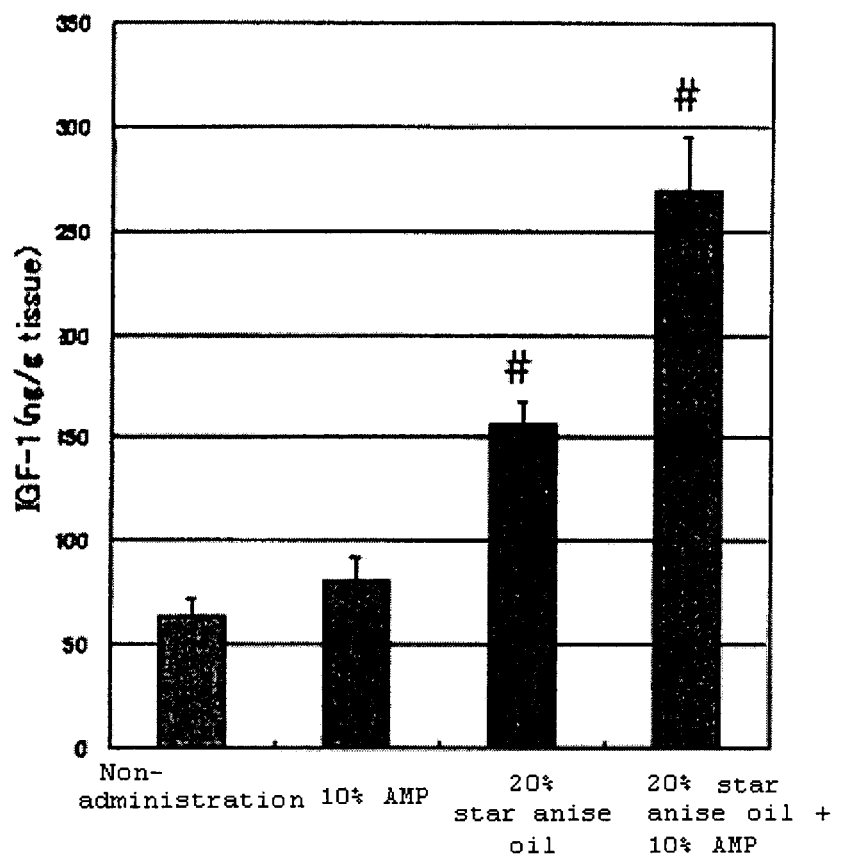
FIG. 1a is a graph showing the effects of an essential oil (star anise oil) and AMP on the amount of IGF-1 in the skin (in the figure, # indicates $P<0.05$).
Figure 1B:
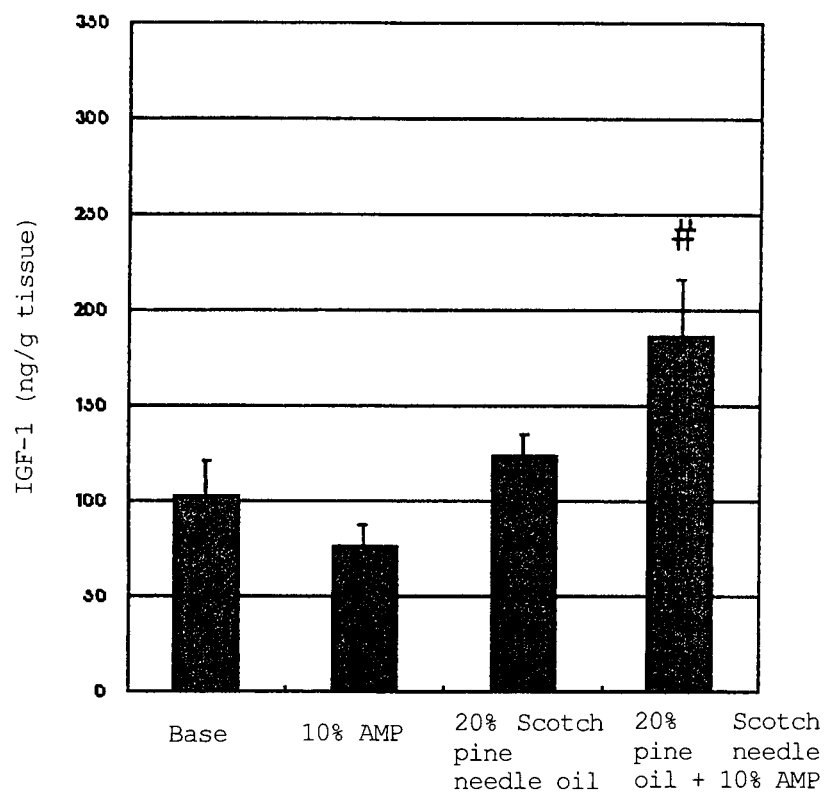
FIG. 1b is a graph showing the effects of an essential oil (Scotch pine oil) and AMP on the amount of IGF-1 in the skin (in the figure, # indicates $P<0.05$).
Figure 1C:
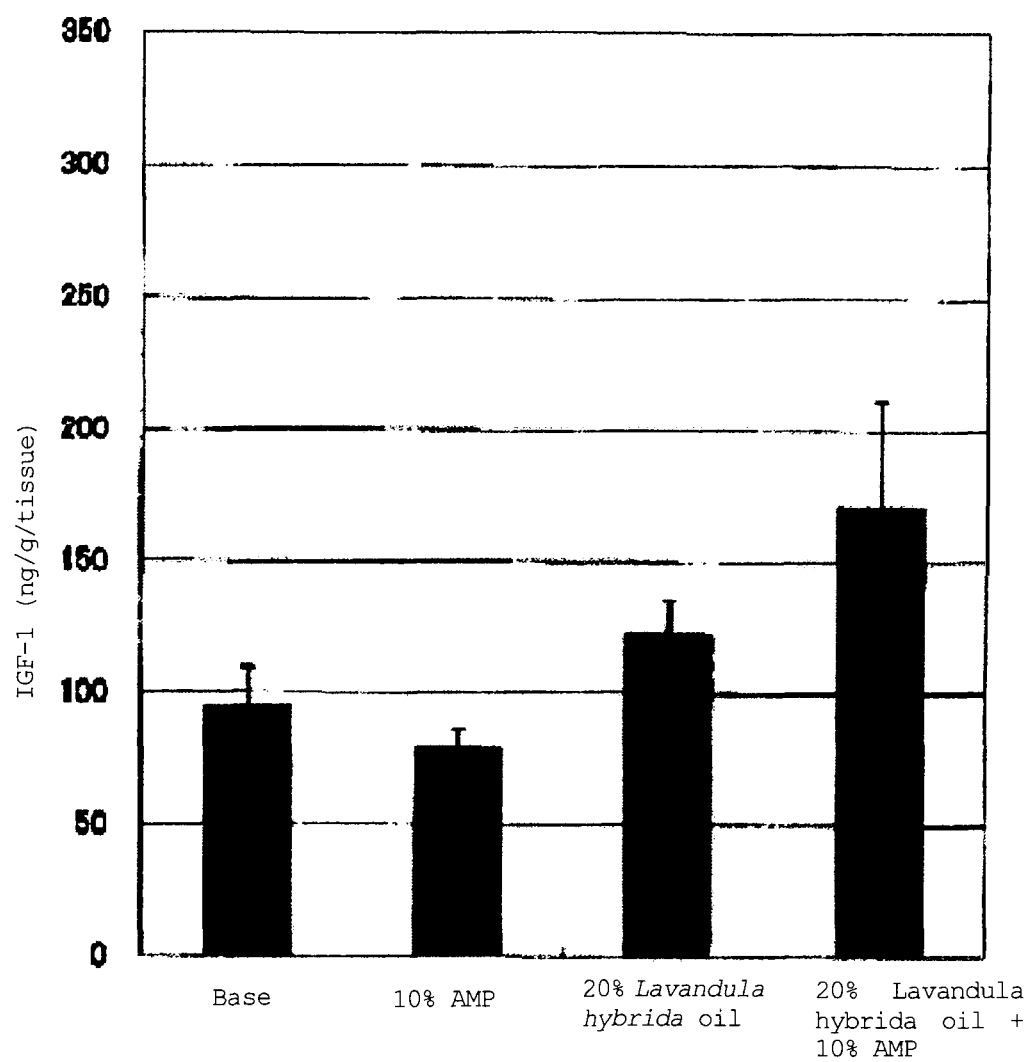
FIG. 1c is a graph showing the effects of an essential oil (*Lavandula hybrida* oil) and AMP on the amount of IGF-1 in the skin.
Figure 2:
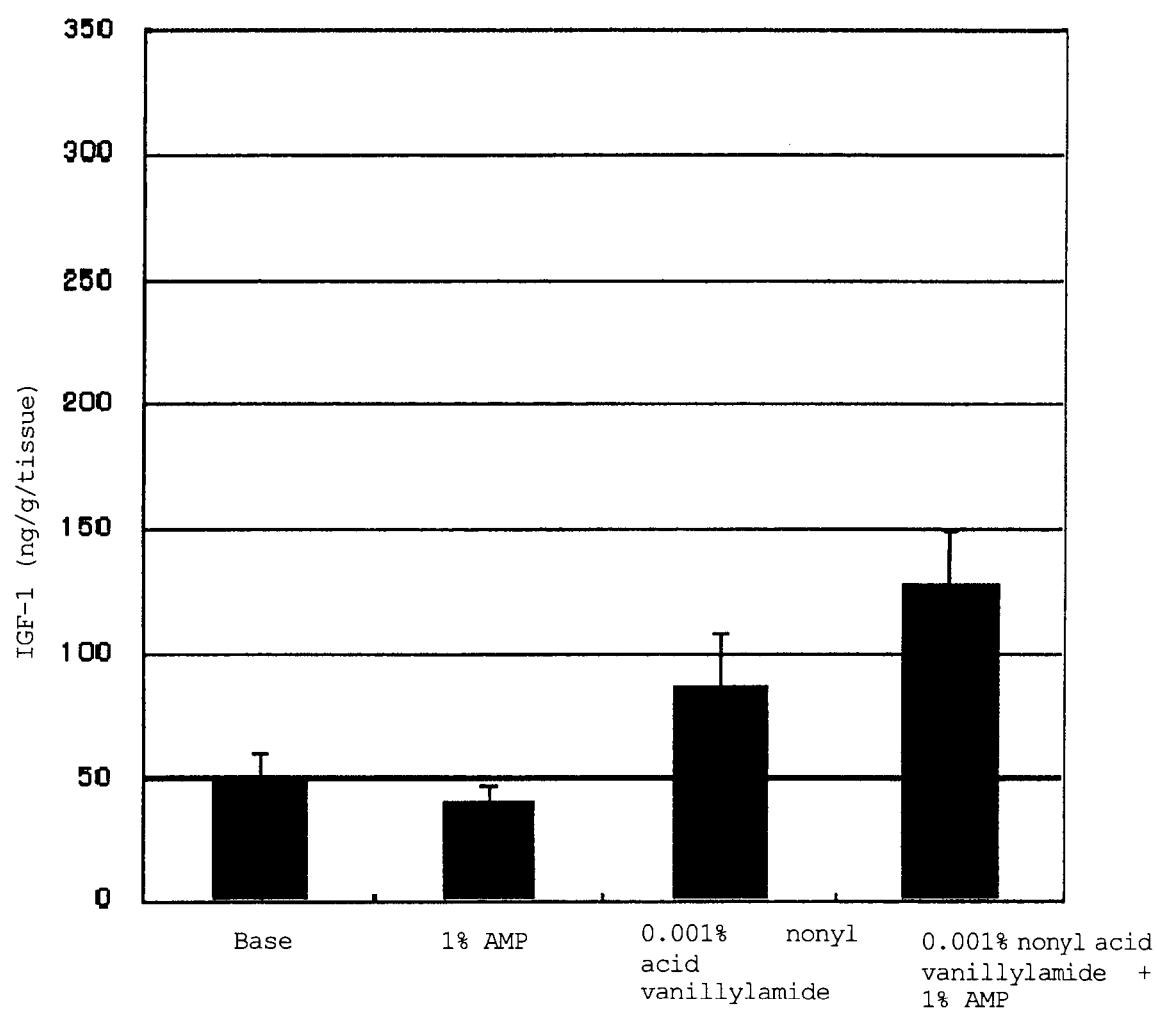
FIG. 2 is a graph showing the increasing effects of nonyl acid vanillylamide and AMP on the amount of IGF-1 in the skin.
Figure 3A:
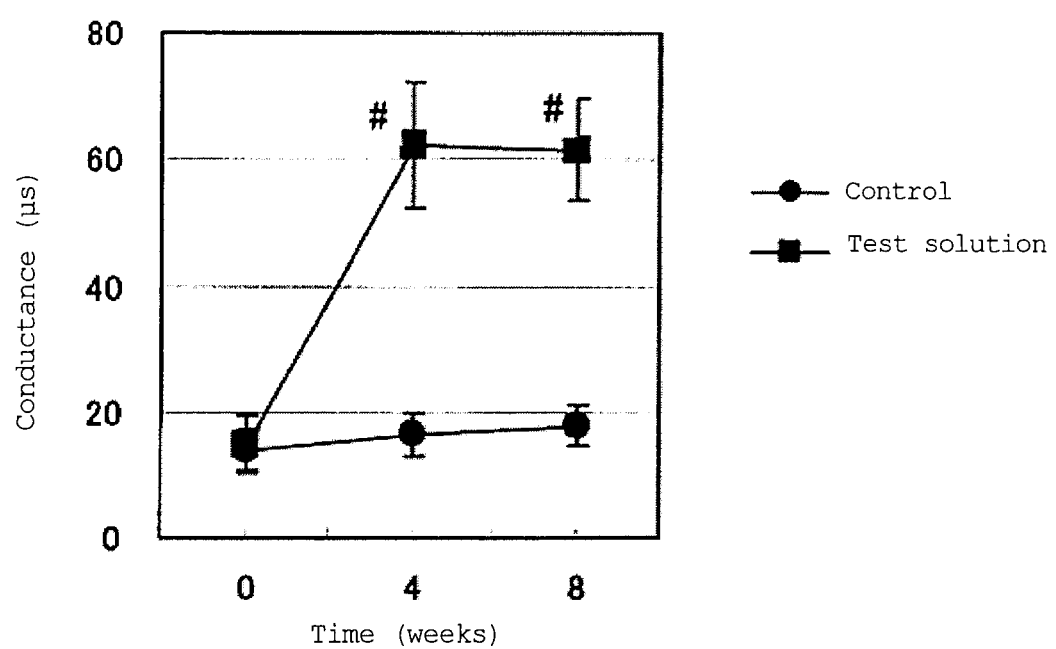
FIG. 3a is a graph showing a change in the stratum corneum water content in Experimental Example 4 (in the figure, # indicates $P<0.05$).
Figure 3B:
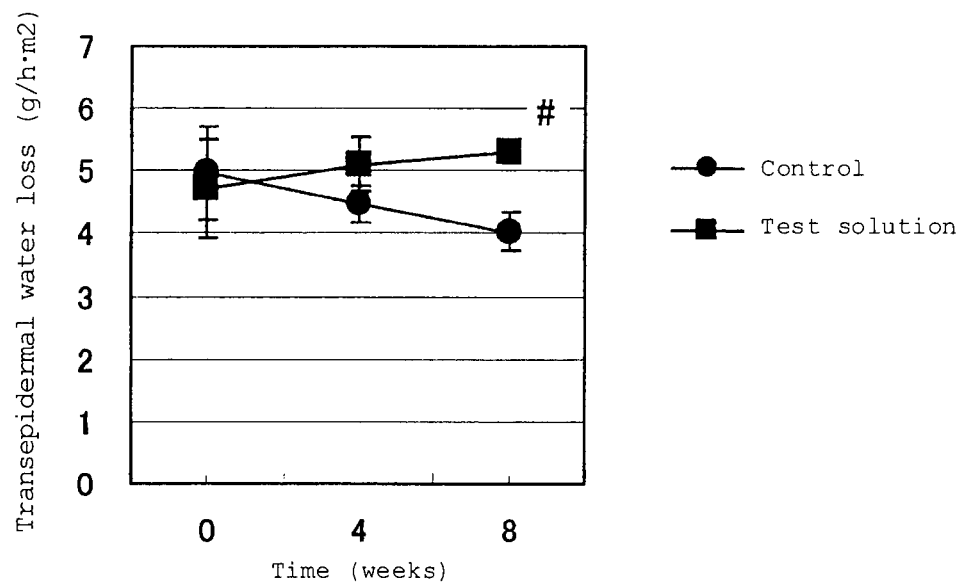
FIG. 3b is a graph showing a change in the transepidermal water loss in Experimental Example 4 (in the figure, # indicates $P<0.05$).
Figure 3C:
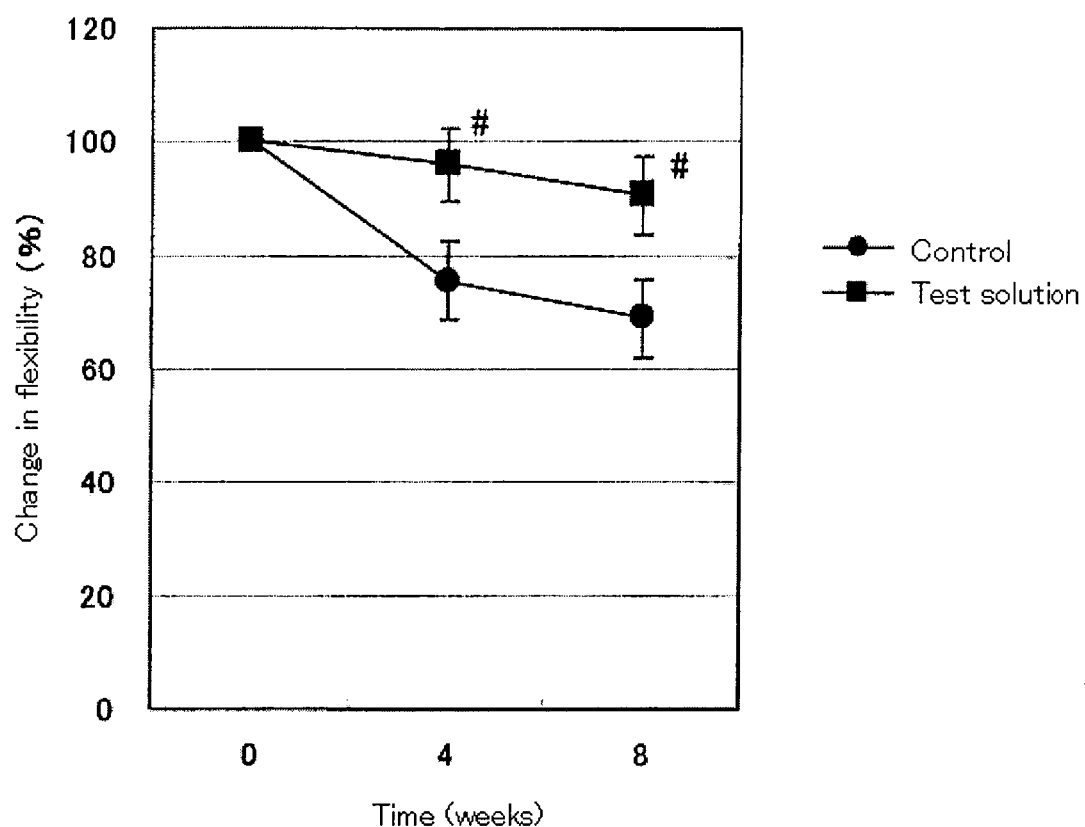
FIG. 3c is a graph showing a change in skin flexibility in Experimental Example 4 (in the figure, # indicates $P<0.05$).
Figure 3D:
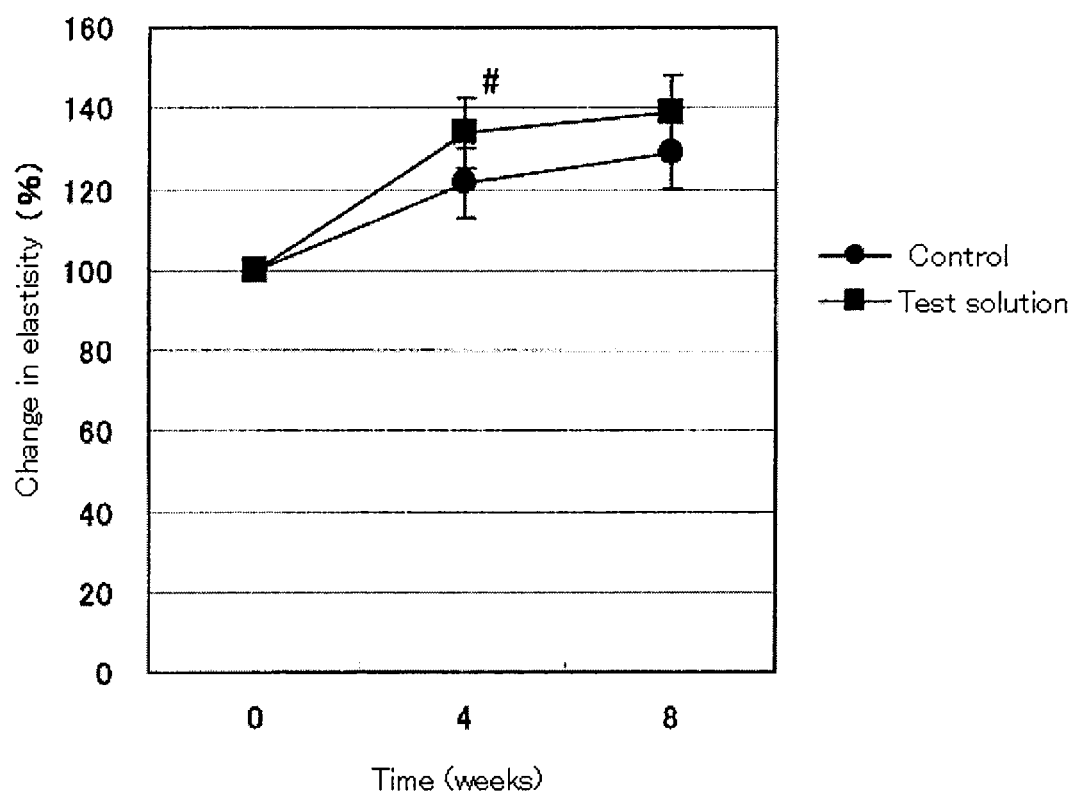
FIG. 3d is a graph showing a change in skin elasticity in Experimental Example 4 (in the figure, # indicates $P<0.05$).
Figure 3E:
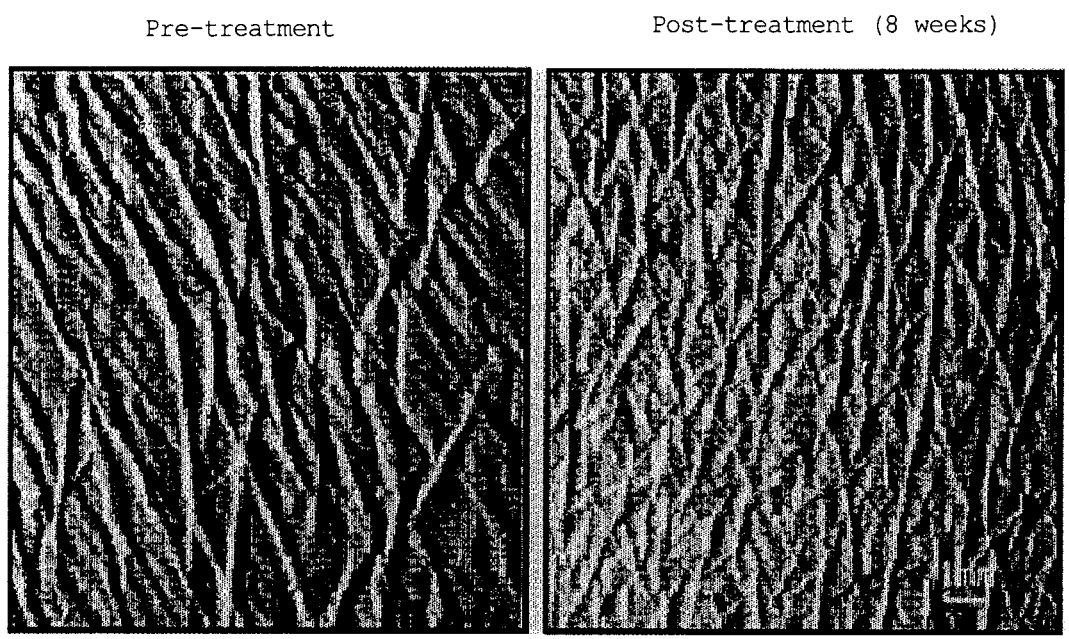
FIG. 3e is a picture showing a change in fineness of skin texture in Experimental Example 4.
Figure 4A:
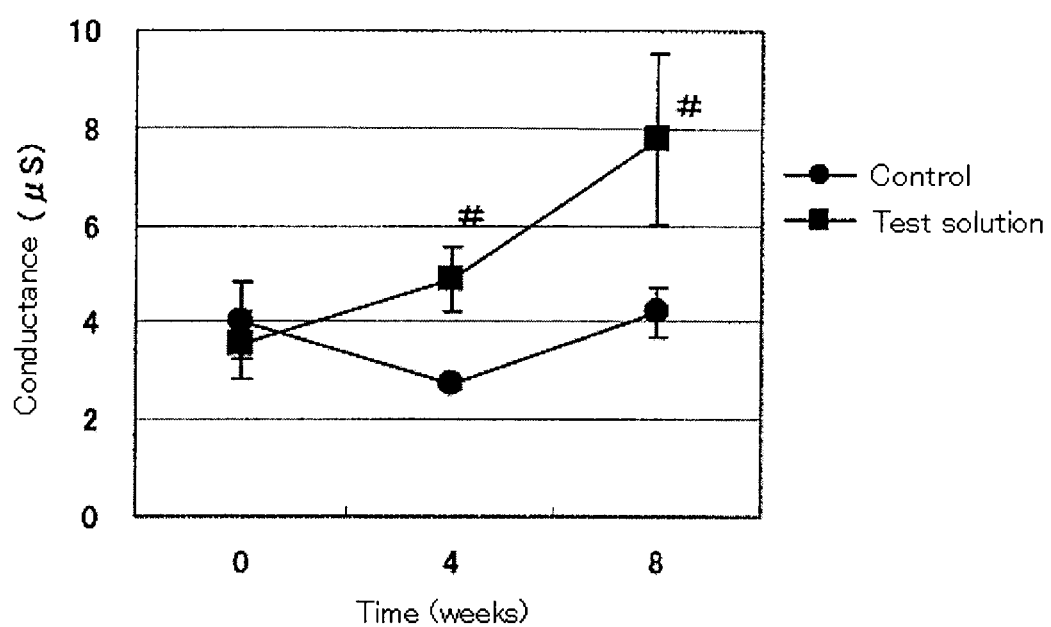
FIG. 4a is a graph showing a change in the stratum corneum water content in Experimental Example 5 (in the figure, # indicates $P<0.05$).
Figure 4B:
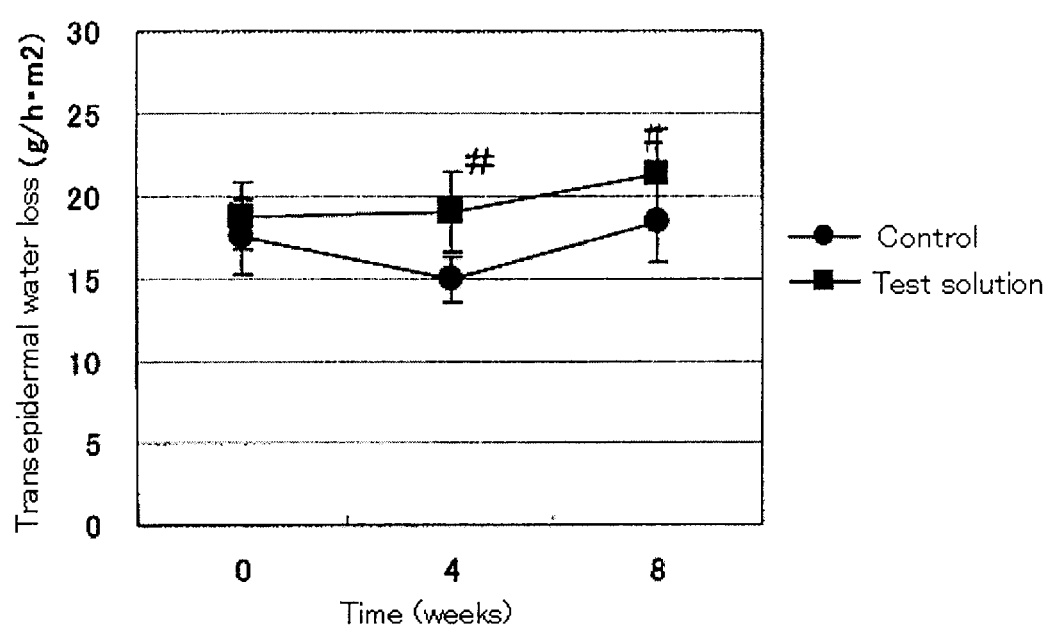
FIG. 4b is a graph showing a change in the transepidermal water loss in Experimental Example 5 (in the figure, # indicates $P<0.05$).
Figure 4C:
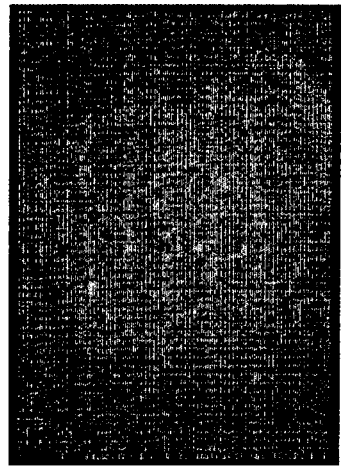
FIG. 4c shows enlarged pictures of the heel after the eighth week of application and non-application of the test solution in Experimental Example 5.
Figure 4C:
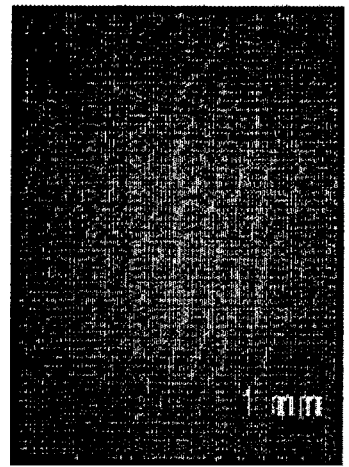
Figure 5A:
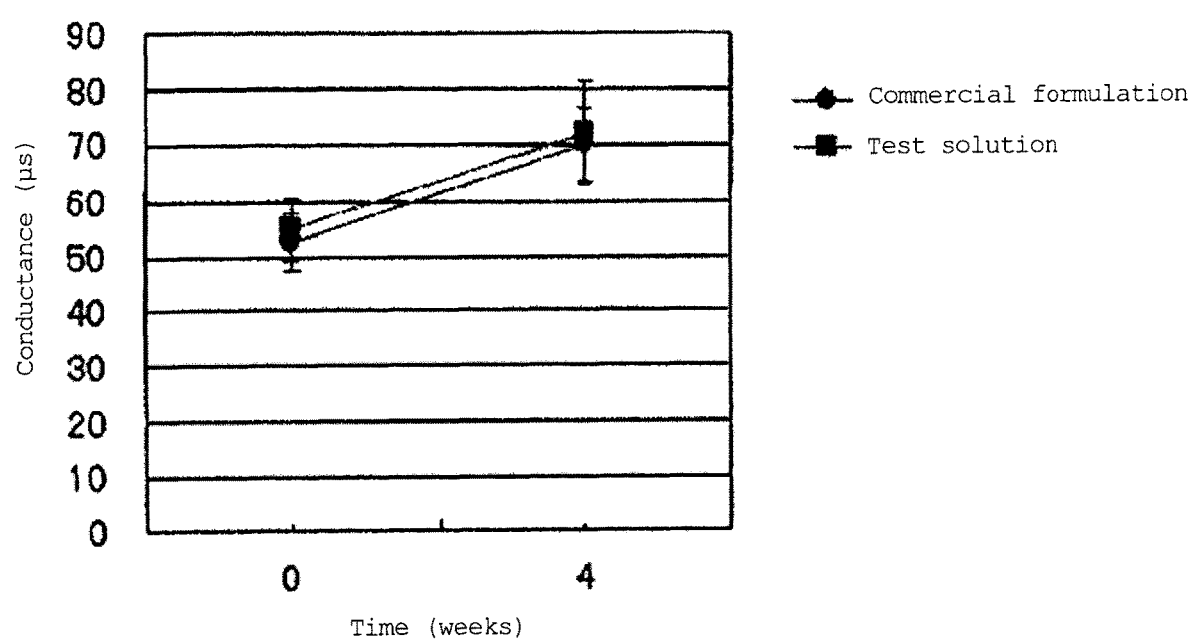
FIG. 5a is a graph showing a change in the stratum corneum water content in Experimental Example 6.
Figure 5B:
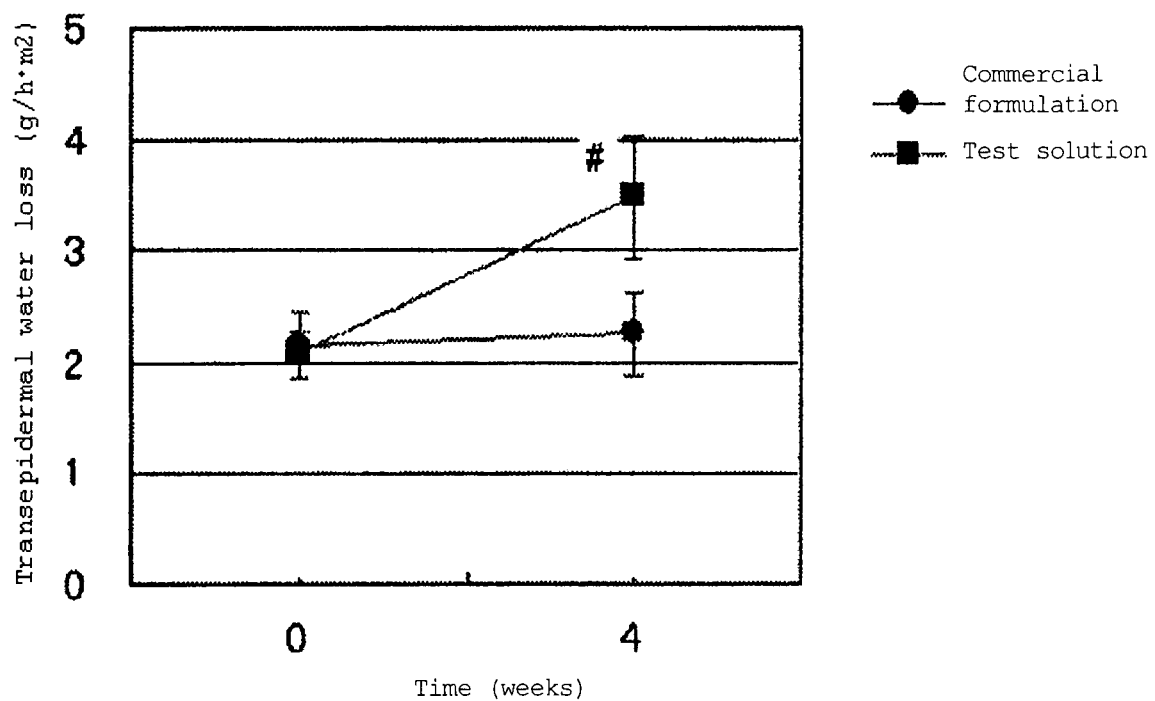
FIG. 5b is a graph showing a change in the transepidermal water loss in Experimental Example 6 (in the figure, # indicates $P<0.05$).

The invention claimed is:

1. A composition for external application to human skin comprising:
   Component (A): an effective amount of essential oil extract comprising a mixture of star anise oil, Scotch pine oil, and *Lavandula hybrida* oil for increasing IGF-1 secretion,
   Component (B): an effective amount of at least one member selected from the group consisting of adenosine monophosphates and salts thereof for increasing IGF-1 secretion, and
   Component (C): at least one member selected from the group consisting of an antiseptic, a humectant, an antioxidant and a sequestering agent;
   wherein the composition is in a form selected from the group consisting of an emulsion, a cream, a sheet, a lipstick, a lotion, and a sunscreen; and
   wherein Component (A) is present in an amount from about 0.0001 to 25 wt %, and Component (B) is present in an amount from about 0.1 to 10 wt % of the composition.

2. The composition according to claim 1, wherein Component (A) is an essential oil extract comprising a mixture of star anise oil, cedar leaf oil, Atlas cedar oil, *Lavandula hybrida* oil, lime oil, peppermint oil, Scotch pine oil, rosemary oil and turpentine oil.

3. The composition according to claim 1, wherein Component (B) is adenosine 5'-monophosphate or a salt thereof.

4. The composition according to claim 1, wherein Component (A) is present in an amount of 0.0000005 to 1,000 parts by weight per part by weight of Component (B).

5. The composition according to claim 1, wherein the composition is in the form of a cosmetic composition, quasi-drug, or pharmaceutical composition.

6. A method of producing an externally applied composition for the skin, comprising combining the following:
   Component (A): an effective amount of essential oil extract comprising a mixture of star anise oil, Scotch pine oil, and *Lavandula hybrida* oil for increasing IGF-1 secretion,
   Component (B): an effective amount of at least one member selected from the group consisting of adenosine monophosphates and salts thereof for increasing IGF-1 secretion, and
   Component (C): at least one member selected from the group consisting of an antiseptic, a humectant, an antioxidant and a sequestering agent;
   wherein the composition is produced in a form selected from the group consisting of an emulsion, a cream, a sheet, a lipstick, a lotion, and a sunscreen; and
   wherein Component (A) is present in an amount from about 0.0001 to 25 wt %, and Component (B) is present in an amount from about 0.1 to 10 wt % of the composition.

7. A method of stimulating IGF-1 secretion in the skin, comprising applying to the skin a composition comprising:
   Component (A): an effective amount of essential oil extract comprising a mixture of star anise oil, Scotch pine oil, and *Lavandula hybrida* oil,
   Component (B): an effective amount of at least one member selected from the group consisting of adenosine monophosphates and salts thereof, and Component (C): at least one member selected from the group consisting of an antiseptic, a humectant, an antioxidant and a sequestering agent;
   wherein the composition is in a form selected from the group consisting of an emulsion, a cream, a sheet, a lipstick, a lotion, and a sunscreen; and
   wherein Component (A) is present in an amount from about 0.0001 to 25 wt %, and Component (B) is present in an amount from about 0.1 to 10 wt % of the composition.

* * * * *